(12) United States Patent
Sun et al.

(10) Patent No.: US 10,043,295 B2
(45) Date of Patent: Aug. 7, 2018

(54) RECONSTRUCTION AND COMBINATION OF PET MULTI-BED IMAGE

(71) Applicant: SHENYANG NEUSOFT MEDICAL SYSTEMS CO., LTD., Shenyang (CN)

(72) Inventors: Zhipeng Sun, Shenyang (CN); Shaolian Liu, Shenyang (CN); Dong Han, Shenyang (CN); Ming Li, Shenyang (CN); Ruibing Ma, Shenyang (CN)

(73) Assignee: Shenyang Neusoft Medical Systems Co., Ltd., Shenyang (CN)

( * ) Notice: Subject to any disclaimer, the term of this patent is extended or adjusted under 35 U.S.C. 154(b) by 49 days.

(21) Appl. No.: 15/246,433

(22) Filed: Aug. 24, 2016

(65) Prior Publication Data

US 2017/0103551 A1    Apr. 13, 2017

(30) Foreign Application Priority Data

Oct. 13, 2015 (CN) .......................... 2015 1 0670913

(51) Int. Cl.
*G06K 9/00* (2006.01)
*G06T 11/00* (2006.01)
(Continued)

(52) U.S. Cl.
CPC ............ *G06T 11/006* (2013.01); *A61B 6/037* (2013.01); *A61B 6/5205* (2013.01);
(Continued)

(58) Field of Classification Search
CPC ................ G06T 2207/20221; G06T 2211/424
See application file for complete search history.

(56) References Cited

U.S. PATENT DOCUMENTS 6,462,342 B1    10/2002 Stearns
8,374,413 B2    2/2013 Chen
(Continued)

FOREIGN PATENT DOCUMENTS

CN        1759807 A      4/2006
CN        101080745 A    11/2007
(Continued)

OTHER PUBLICATIONS

Muzic et al (NPL: "PET/MRI—Technical Review", HHS Public ACCESS, Jul. 2014, pp. 30, doi:10.1053/j.ro.2014.10.001.).*

(Continued)

*Primary Examiner* — Oneal R Mistry
(74) *Attorney, Agent, or Firm* — McCoy Russell LLP

(57) ABSTRACT

A method for reconstructing a PET multi-bed image is provided, which may be applied to a PET scan having an axial overlapping region existed between every two adjacent beds. According to an example of the method, a combined set of PET projection data for at least two beds may be obtained by combining a set of PET projection data for at least two successive beds together in such a manner that two sets of PET projection data corresponding to an axial overlapping region between every two adjacent beds are added up. And then, a PET image for at least two beds may be reconstructed based on an image reconstruction iteration model and the combined set of PET projection data for the plurality of beds.

16 Claims, 9 Drawing Sheets

(51) Int. Cl.
*G01T 1/29* (2006.01)
*G06T 3/40* (2006.01)
*A61B 6/03* (2006.01)
*A61B 6/00* (2006.01)

(52) U.S. Cl.
CPC .......... *G01T 1/2985* (2013.01); *G06T 3/4038* (2013.01); *G06T 11/005* (2013.01); *G06T 11/008* (2013.01); *A61B 6/5241* (2013.01); *G06T 2200/32* (2013.01); *G06T 2207/10104* (2013.01); *G06T 2207/20221* (2013.01); *G06T 2210/41* (2013.01); *G06T 2211/424* (2013.01)

(56) References Cited

U.S. PATENT DOCUMENTS

| | | | |
|---|---|---|---|
| 8,509,514 | B2 | 8/2013 | Chen |
| 2003/0004405 | A1* | 1/2003 | Townsend ............... A61B 6/032 600/407 |
| 2007/0278410 | A1 | 12/2007 | Cho et al. |
| 2009/0238337 | A1 | 9/2009 | Wang |
| 2011/0038452 | A1* | 2/2011 | Moghe .................. G06T 11/006 378/19 |
| 2011/0079722 | A1 | 4/2011 | Gagnon |
| 2012/0121062 | A1 | 5/2012 | Sowards-Emmerd et al. |
| 2014/0016740 | A1 | 1/2014 | Gotman |
| 2015/0003708 | A1 | 1/2015 | Prevrhal et al. |
| 2016/0063741 | A1* | 3/2016 | Ye ......................... G06T 11/005 382/131 |
| 2017/0084025 | A1* | 3/2017 | Lyu ....................... G06T 7/0012 |
| 2018/0035959 | A1* | 2/2018 | Kim .................... A61B 6/5241 |
| 2018/0049710 | A1* | 2/2018 | Wilson .................. A61B 6/482 |

FOREIGN PATENT DOCUMENTS

| | | |
|---|---|---|
| CN | 103593868 A | 2/2014 |
| CN | 103745488 A | 4/2014 |
| CN | 103955899 A | 7/2014 |
| CN | 104408763 A | 3/2015 |
| CN | 104574459 A | 4/2015 |
| CN | 104599301 A | 5/2015 |
| WO | 2010063482 A1 | 6/2010 |
| WO | 2014024009 A2 | 2/2014 |

OTHER PUBLICATIONS

Zhou Jian et al.; Row-action SAGE algorithm for PET image reconstruction; Journal of Southeast University; Dec. 2004; pp. 467-470; vol. 20 No. 4; Nanjing, CN.
Li Zhenwei et al.; An Overview of PET/CT Image Reconstruction Techniques; Chinese Journal of Medical Instrumentation; 2011; pp. 53-57; Issue 1.
State Intellectual Property Office of the People's Republic of China, Office Action Issued in Application No. 201510670913.9, Oct. 25, 2017, 12 pages. (Submitted with Partial Translation).

* cited by examiner

RECONSTRUCTION AND COMBINATION OF PET MULTI-BED IMAGE

CROSS-REFERENCE TO RELATED APPLICATIONS

The present application claims priority to Chinese Patent Application No. 201510670913.9, filed on Oct. 13, 2015, the entire contents of which are hereby incorporated by reference for all purposes.

BACKGROUND

The present disclosure is directed to reconstruction and combination of a Positron Emission Tomography (PET) multi-bed image.

PET is a medical imaging technique for observing internal physiological metabolism of a subject. The detection principle of PET may be as follows. First, particular radiopharmaceuticals may be injected into the subject, and as these particular radiopharmaceuticals continue to be accumulated in tissues of the subject, an intensity of radioactivity in these tissues will continue to be increased. Then, a PET detector system may be used for capturing back-to-back γ photon pairs released during the decay process of these particular radiopharmaceuticals so as to form raw data. After that, a particular calibration algorithm and a particular reconstruction algorithm may be used for obtaining a tomographic image from the raw data, wherein the tomographic image may represent a distribution of these particular radiopharmaceuticals within the subject and be used to reflect the real physiological metabolism of the subject.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

BRIEF DESCRIPTION OF DRAWINGS

Features of the present disclosure are illustrated by way of example and not limited in the following figures, in which like numerals indicate like elements, in which.

DETAILED DESCRIPTION

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures may have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

During each PET scan process, a PET detector system is stationary relative to a subject lying on a scanning bed, and thus each PET scan may be called a position of bed (hereinafter the position of bed may be referred to as "a bed"). Due to limited axial extent of the PET detector system, a multi-bed scan is generally necessary when a whole body or a large area of the subject is scanned. For example, 5-8 beds of PET scans may be required for a whole body scanning of the subject based on the subject's height and the axial coverage of the PET detector system. For two adjacent beds, the scanning bed may move a distance along an axial direction (hereinafter, this distance may be referred to as "a stepping distance of the scanning bed") to ensure that the two adjacent beds may be partly but not wholly overlapped, i.e., a certain axial overlap may exist between the two adjacent beds. It is because that a set of data collected by a PET scan may be uneven in the axial direction. For example, a set of PET data collected on a layer may be less than the layer closer to an axial edge, this may result in that image noise on a layer closer to an axial edge is higher than image noise on another layer closer to center. If a certain axial overlap does not exist between two adjacent beds during data collection, obvious or unbearable noises may appear in the images of two or three layers located at the junction of two adjacent beds. Therefore, in order to reduce the noises, a certain axial overlap may exist between two adjacent beds.

Figure 1:
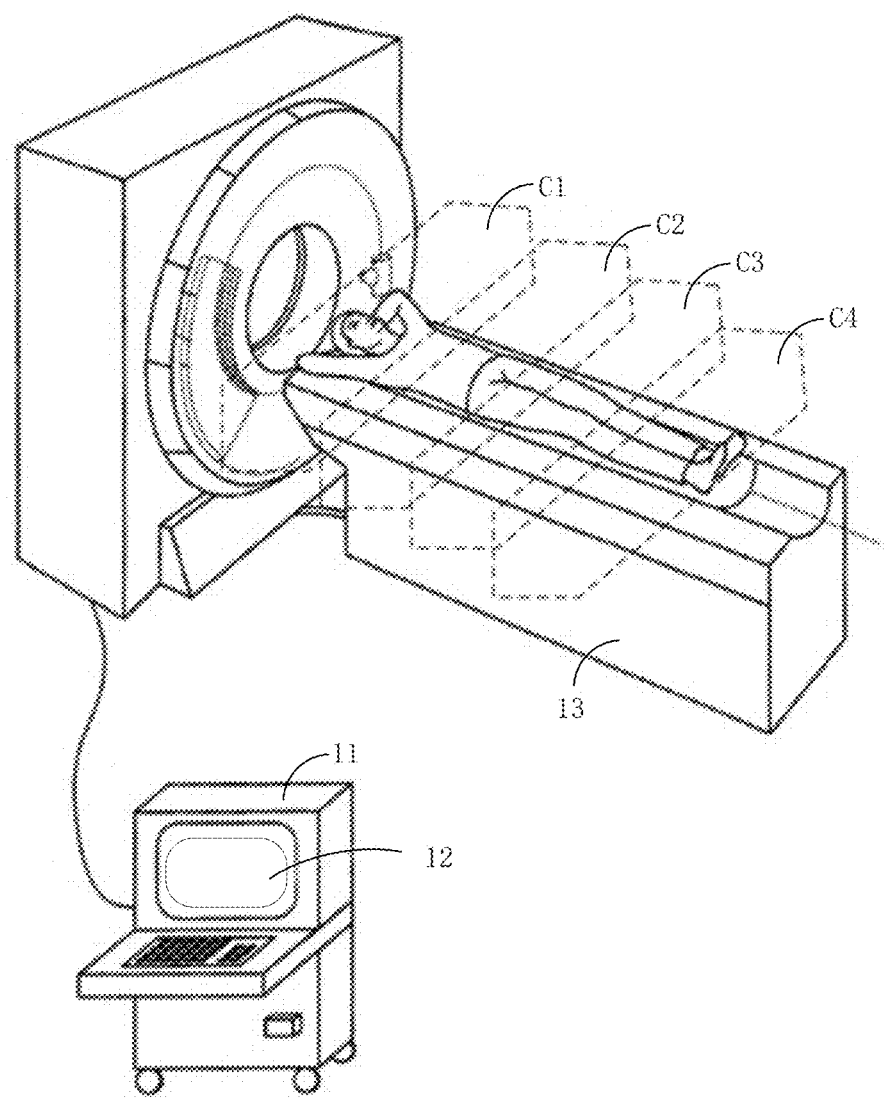
FIG. 1 is a system architecture diagram of a PET scan system according to an example of the present disclosure.

Referring to FIG. 1. FIG. 1 is a system architecture diagram of a PET scan system according to an example of the present disclosure. When a PET whole body scan is performed on a subject lying on a scanning bed, it may be scanned based on beds. For example, different beds may correspond to different portions of the subject, and scan images of a plurality of beds may be combined to form a whole body scan image of the subject.

Figure 2:
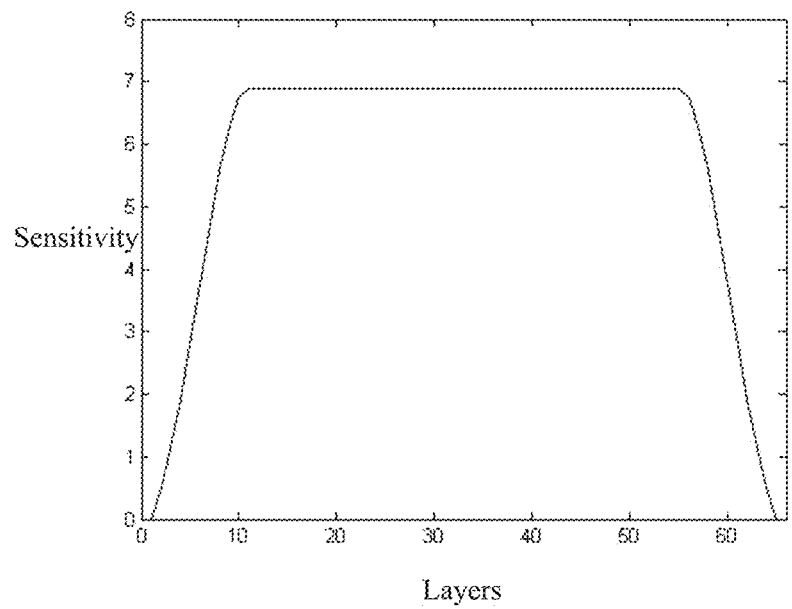
FIG. 2 is a schematic diagram showing a relationship between an axial sensitivity and layers when collecting data by a PET scan.
Figure 3:
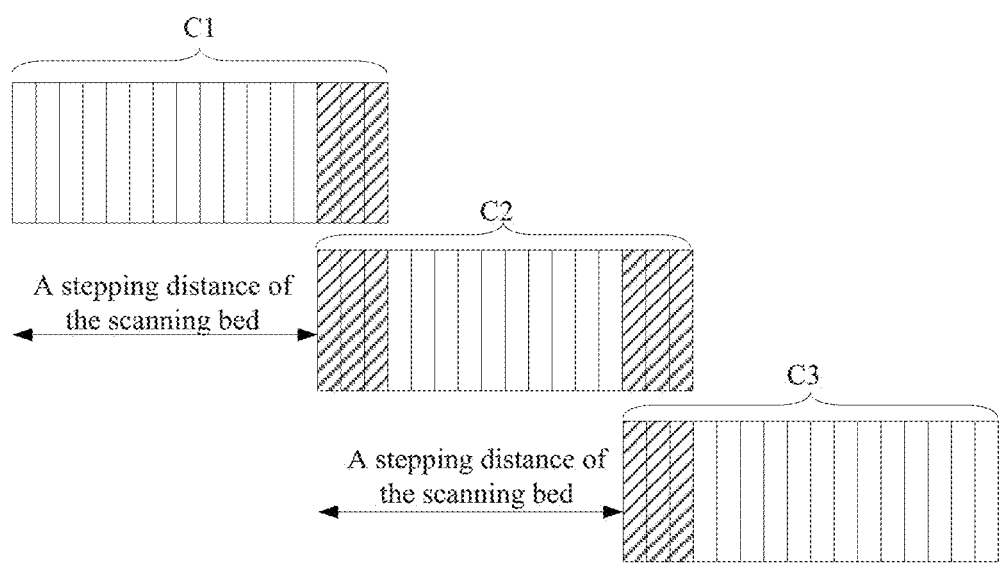
FIG. 3 is a schematic diagram showing a stepping distance of PET scanning beds and overlapping layers.

In FIG. 1, four scanning beds are shown in this example, which may include the scanning bed C1, the scanning bed C2, the scanning bed C3, and the scanning bed C4, respectively. Certainly, those skilled in the art should appreciate that, in specific implementation, the number of the beds may not be limited to 4. A PET scan may be performed according to the sequence of the scanning beds C1 to C4 one by one. These four scanning beds C1-C4 may be used for scanning different body portions of the subject, respectively. For example, the scanning bed C1 may be used for scanning the portion above the neck of the subject, the scanning bed C2 may be used for scanning the chest and abdomen portion of the subject, the scanning bed C3 may be used for scanning the thigh portion of the subject, and the scanning bed C4 may be used for scanning the leg and foot portion of the subject. Be noted that, in order to reduce image noises, a certain axial overlapping region may exist between every two adjacent beds. Since a set of PET projection data collected by a PET scan may be uneven in the axial direction, the set of PET data collected on a layer may be less than the layer closer to an axial edge. Referring to FIG. 2. FIG. 2 is a schematic diagram showing a relationship between an axial sensitivity and layers when collecting data by a PET scan. This may result in that PET image noises on a layer closer to an axial edge is higher than image noise on another layer closer to center. If a certain axial overlap does not exist between two adjacent beds during data collection, obvious or unbearable noises may appear in the scan images of a plurality of layers located at the junction of two adjacent beds. Therefore, even if the overlapping layers will make the number of PET scanning beds increase and the scanning efficiency reduce, a certain number of overlapping layers are usually applied during the PET multi-bed scan process, in order to try to achieve an optimum balance between the scanning efficiency and the image quality. Referring to FIG. 3. FIG. 3 is a schematic diagram showing a stepping distance of PET scanning beds and overlapping layers. In FIG. 3, the scanning bed C1, the scanning bed C2, and the scanning bed C3 may represent a first scanning bed, a second scanning bed, and a third scanning bed of the PET detector system, respectively. In this example, each rectangular region may represent a scanning layer, a length of the arrow may represent a stepping distance of the scanning bed, and a shaded region may represent an overlapping region between adjacent beds.

In an example, before a PET whole body scan is performed on the subject, scanning parameters for each of the scanning beds may usually be determined in advance, such as a scanning time. After setting the scanning parameters, the PET scan device may scan the subject according to the scanning parameters. Please keep referring to FIG. 1. During the scanning process, an operating doctor may use the control device 11 to set the scanning parameters. The control device 11 may be a computer. Control software 12 for controlling the PET device may be installed on the control device 11, thus the operating doctor may set scanning parameters of the PET device through a human-machine interface of the control software 12, and then control the scan of the PET device.

In accordance with the PET scan system shown in FIG. 1, a method for reconstructing a PET multi-bed image is provided in this example of the present disclosure. The method for reconstructing a PET multi-bed image may be based on an OSEM (Ordered-Subset Expectation Maximization) algorithm. The OSEM algorithm may describe a matching between the PET image and the PET projection data by establishing a Poisson-Probability-Model-Based likelihood function, such as the following formulas (1) and (2). Then, an iterative solution may be used for obtaining a global maximum value of the likelihood function as a final PET image.

Figure 4:
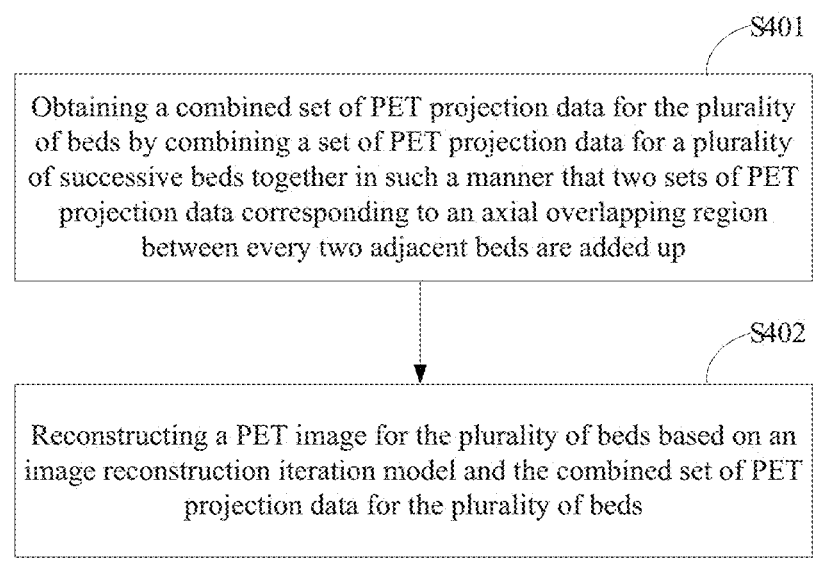
FIG. 4 is a flowchart illustrating the procedures of a method for reconstructing a PET multi-bed image according to an example of the present disclosure.

Referring to FIG. 4. FIG. 4 is a flowchart illustrating the procedures of a method for reconstructing a PET multi-bed image according to an example of the present disclosure. As shown in FIG. 4, the method for reconstructing a PET multi-bed image may include the following blocks S401-S402.

At block S401, a combined set of PET projection data for the plurality of beds may be obtained by combining a set of PET projection data for a plurality of successive beds together in such a manner that two sets of PET projection data corresponding to an axial overlapping region between every two adjacent beds may be added up.

In an example, an added set of PET projection data corresponding to the axial overlapping region between every two adjacent beds for the plurality of beds may be obtained by directly adding up two sets of PET projection data corresponding to the axial overlapping region between the two adjacent beds. After that, the combined set of PET projection data for the plurality of beds may be obtained by axially splicing a set of PET projection data corresponding to an axial non-overlapping region between each of the plurality of beds and the added set of PET projection data corresponding to the axial overlapping region between every two adjacent beds together.

In the following, three successive beds are explained as an example. The three successive beds may include a first bed C1, a second bed C2, and a third bed C3, wherein the set of PET projection data D1 for the first bed C1 may be {d11, d12, d13, d14}, the set of PET projection data D2 for the second bed C2 may be {d21, d22, d23, d24}, and the set of PET projection data D3 for the third bed C3 may be {d31, d32, d33, d34}. In an example, a position corresponding to the data d13 axially may overlap a position corresponding to the data d21, a position corresponding to the data d14 axially may overlap a position corresponding to the data d22, and a position corresponding to the data d24 may axially overlap a position corresponding to the data d31. In this case, the data d13 and the data d21 may be directly added up, and the data d14 and the data d22 may be directly added up, so as to obtain an added set of PET projection data for the axial overlapping region between the first bed C1 and the second bed C2. Next, the data d24 and the data d31 may be directly added up, so as to obtain an added set of PET projection data for the axial overlapping region between the second bed C2 and the third bed C3. Then, the set of PET projection data for the first bed C1, the second bed C2, and the third bed C3 may be combined together, so as to obtain a combined set of PET projection data D123, which is {d11, d12, d13+d21, d14+d22, d23, d24+d31, d32, d33, d34}.

Through the block S401, the set of PET projection data obtained through a plurality of scanning processes may be combined into a set of PET projection data axially having a relatively long range, which may be equivalent to the set of PET projection data obtained through a scanning process axially having a large range.

Be noted that, the block S401 may be performed after obtaining the set of PET projection data corresponding to all of the plurality of beds, or may be performed after obtaining the set of PET projection data corresponding to every two adjacent beds.

Be noted that, in this block S401, two sets of PET projection data corresponding to the axial overlapping region between every two adjacent beds may be directly added up, respectively, so as to combine a set of PET projection data for at least two successive beds together. Since the two sets of projection data corresponding to the axial overlapping region may be directly added up without performing any process (such as, a weighting process), this make the combined set of PET projection data still be able to maintain a Poisson distribution characteristic, thereby ensuring the quality of the PET image.

At block S402, a PET image for the plurality of beds is reconstructed based on an image reconstruction iteration model and the combined set of PET projection data for the plurality of beds.

Be noted that, the adopted image reconstruction iteration model may be a commonly-used PET image reconstruction iteration model in the art. For example, the image reconstruction iteration model may be expressed according to the following formula (1):

$$\lambda_s^{(k,m+1)} = \frac{\lambda_s^{(k,m)}}{\sum_{n=1}^{n_{Frames}} \sum_{t \in S_m} A_{tn} a_{ts}} \sum_{n=1}^{n_{Frames}} \sum_{t \in S_m} \frac{A_{tn} Y_{tn} a_{ts}}{\sum_{S'} A_{tn} a_{ts'} \lambda_{s'}^{(k,m)}} \quad (1)$$

Herein $\lambda$ represents the PET image, k represents an iteration number, m represents a serial number of a subset, s and s' represent an index value of pixels of the PET image $\lambda$, and a range of the index value s is the same as a range of the index value s';

Y represents the set of PET projection data, and t represents an index value of the set of PET projection data Y;

A represents a correction factor, which may include a random matching random correction factor for the correction data, a normalization correction factor for correcting crystal efficiencies to a consistent crystal efficiency, an attenuation correction factor and a scatter correction factor for compensating Compton effect caused by gamma photons inside the field of view of the detector.

$n_{Frames}$ represents the number of beds corresponding to the set of combined PET projection data, and n represents a serial number of a bed;

Sm represents a set of data corresponding to the m-th subset, and S' also represents the set of data corresponding to the m-th subset; wherein S' is embedded in Sm in the formula (1), thus different symbols are adopted to show the differences between them; and $a_{ts}'$ represents the probability that the data transmitted from the s-th pixel is received at the t-th response line, and $a_{ts}$ also represents the probability that the data transmitted from the s-th pixel is received at the t-th response line.

In this case, the response line is the smallest unit of the set of PET projection data, and a response line may correspond to a segment connecting two crystals of the PET detector system. Thus, the set of PET projection data may be considered to be enumerated by a plurality of response lines.

The data transmitted from the s-th pixel and received at the t-th response line means that the data transmitted from the s-th pixel results in positron annihilation phenomenon occurred at somewhere in the t-th response line, that is to say, positrons and negative electrons collide and release a pair of back-to-back gamma photons emitted along the direction of the response line.

However, the image reconstruction iteration model shown in the above formula (1) may have the following disadvantages.

In the image reconstruction iteration model shown in the above formula (1), the combination $$\sum_{n=1}^{n_{Frames}}$$

of the set of PET projection data for the plurality of beds is performed after calculating the ratio $$\frac{A_{tn} Y_{tn} a_{ts}}{\sum_{S'} A_{tn} a_{ts'} \lambda_{s'}^{(k,m)}},$$

and thus the amount of data statistics for calculating the ratio is too small, which is unfavourable for reducing image noises.

In order to reduce calculations during a PET image reconstruction process and to improve the signal-to-noise ratio of a PET image, a new PET image reconstruction iteration model may be adopted in this case. The new PET image reconstruction iteration model may be expressed according to the following formula (2):

$$\lambda_s^{(k,m+1)} = \frac{\lambda_s^{(k,m)}}{\sum_{n=1}^{h} \sum_{t \in Sm} A_{tn} a_{ts}} \sum_{t \in Sm} \frac{\sum_{n=1}^{h} A_{tn} N_{tn} Y_{tn} a_{ts}}{\sum_{n=1}^{h} \left[ A_{tn} \left( \sum_{S'} a_{ts'} \lambda_{s'}^{(k,m)} + S_{tn} \right) \right] N_{tn} + R_{tn}} \quad (2)$$

Herein $\lambda$ represents the reconstructed PET image, k represents an iteration number, and m represents a serial number of a subset;

h represents the number of beds corresponding to the combined set of PET projection data, h≥2, and h is an integer; n represents a serial number of a bed, n∈{1, 2, 3, . . . , h}, and n is an integer;

Atn represents an attenuation correction factor of the t-th response line in the n-th bed;

ats represents the probability that the data transmitted from the s-th pixel is received at the t-th response line;

ats' also represents the probability that the data transmitted from the s-th pixel is received at the t-th response line;

Ytn represents the set of PET projection data of the t-th response line in the n-th bed;

Ntn represents a normalization correction factor of the t-th response line in the n-th bed;

Rtn represents a random correction factor of the t-th response line in the n-th bed;

Stn represents a scatter correction factor of the t-th response line in the n-th bed; and Sm represents a set of data corresponding to the m-th subset, and S' also represents the set of data corresponding to the m-th subset. S' is embedded in Sm in the formula (2), and thus different symbols are adopted to show the differences between them.

In the PET image reconstruction iteration model shown in the above formula (2), the combination $$\sum_{n=1}^{h}$$

of the set of PET projection data for the h successive beds is performed before calculating the ratio $$\frac{\sum_{n=1}^{h} A_{tn} N_{tn} Y_{tn} a_{ts}}{\sum_{n=1}^{h} \left[ A_{tn} \left( \sum_{S'} a_{ts'} \lambda_{s'}^{(k,m)} + S_{tn} \right) \right] N_{tn} + R_{tn}}.$$

Compared to the PET image reconstruction iteration model shown in the above formula (1), the amount of data statistics for calculating the ratio in the PET image reconstruction iteration model shown in the above formula (2) may be increased, which is beneficial for reducing image noises.

According to another example, in the PET image reconstruction iteration model shown in the above formula (2), the set of PET projection data for the h successive beds may be sequentially combined together without simultaneously handling the set of PET projection data of all current beds. For example, setting that h=2. If the third bed has been scanned at the current time, only two sets of PET projection data for the second bed and the third bed may be combined together according to the method shown in the block S401, instead of combining the set of PET projection data for the first bed, the second bed, and the third bed together. Therefore, using the image reconstruction iteration model shown in the above formula (2) for reconstructing the PET image may appropriately reduce computations of the reconstructed images.

As can been seen from the above formula (2), the correction factors of the PET image reconstruction iteration model shown in the above formula (2) may include the normalization correction factor $N_{tn}$, the random correction factor $R_{tn}$, the scatter correction factor $S_{tn}$, and the attenuation correction factor $A_{tn}$, etc. In other words, a portion or all major correction factors may be taken into account during the image reconstruction process in this case. Therefore, a better signal-to-noise ratio of the reconstructed image may be obtained.

Figure 5:
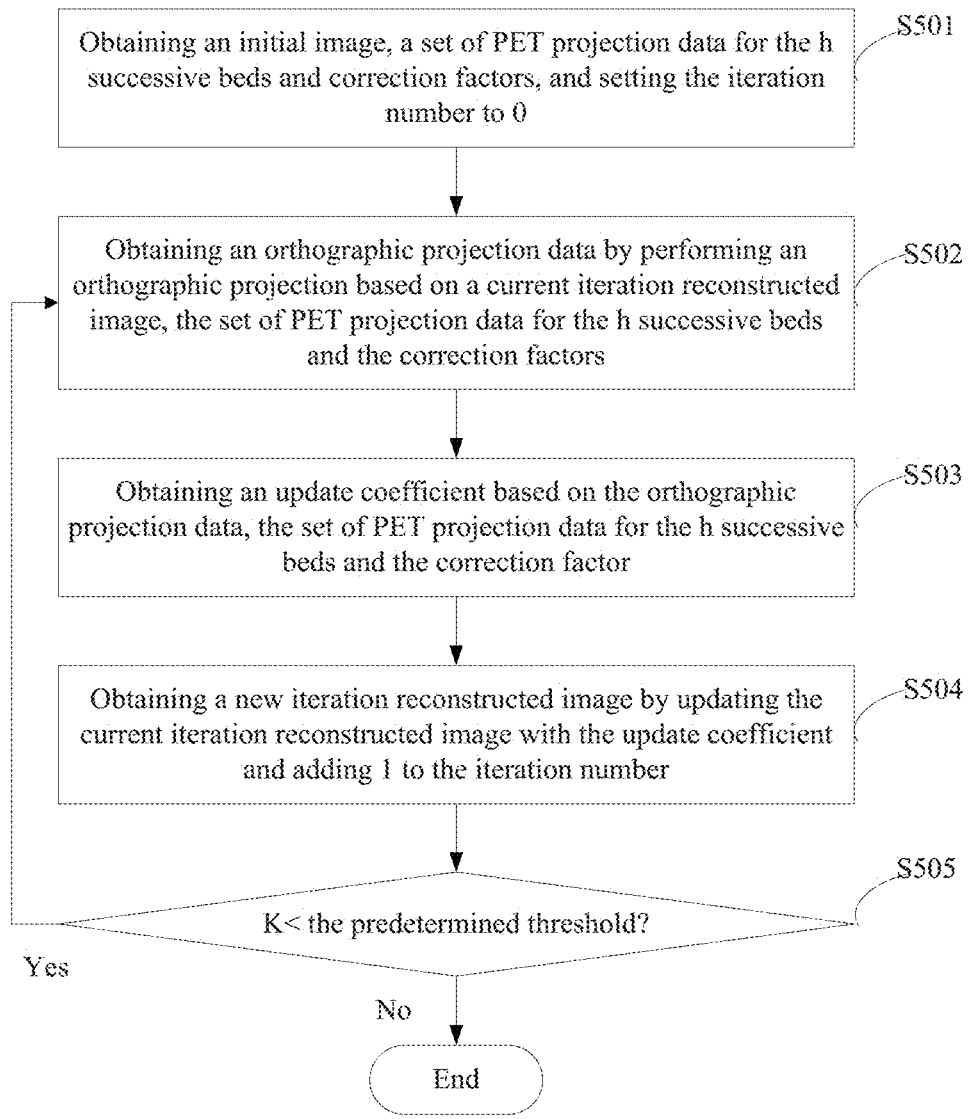
FIG. 5 is a flowchart illustrating the procedures of a method for reconstructing a PET multi-bed image according to another example of the present disclosure.

In a specific example of the present disclosure, the procedures of using the image reconstruction iteration model shown in the above formula (2) to perform a PET image reconstruction on the h successive beds are shown in FIG. 5. Referring to FIG. 5. FIG. 5 is a flowchart illustrating the procedures of a method for reconstructing a PET multi-bed image according to another example of the present disclosure. As shown in FIG. 5, the method for reconstructing a PET multi-bed image may include the following blocks S501-S505.

At block S501, an initial image, a set of PET projection data for the h successive beds and one or more of the correction factors may be obtained, and the iteration number is set to 0.

Be noted that, in this example, the initial image is an initial value of the iteration reconstructed image, which may be a random value or the same value at each reconstruction. In another example, the initial image may be a rough result calculated based on other reconstruction methods.

In this example, the correction factors may include one or more of the normalization correction factor $N_{tn}$, the random correction factor $R_{tn}$, the scatter correction factor $S_{tn}$, and the attenuation correction factor $A_{tn}$, etc. In other words, all major correction factors may be taken into account during the image reconstruction process in this case. Therefore, a better signal-to-noise ratio of the reconstructed image may be obtained.

At block S502, an orthographic projection data is obtained by performing an orthographic projection based on a current iteration reconstructed image, the set of PET projection data for the h successive beds, and one or more of the correction factors, wherein about the first iteration (i.e., where the iteration number is set to 0), the current iteration reconstructed image is the initial image.

As a specific example, the formula of the orthographic projection data $y_t$ may be shown as follows:

$$y_t = \sum_{n=1}^{h} \left[ A_{tn} \left( \sum_{S'} a_{ts'} \lambda_{s'}^{(k,m)} + S_{tn} \right) \right] N_{tn} + R_{tn} \quad (3)$$

Herein $\lambda$ represents the reconstructed PET image, k represents the iteration number, and m represents the serial number of a subset;

h represents the number of beds corresponding to the combined PET projection data, h≥2, and h is an integer; n represents the serial number of a bed, n∈{1, 2, 3, ..., h}, and n is an integer;

$A_{tn}$ represents the attenuation correction factor for the t-th response line in the n-th bed;

$a_{ts}'$ represents the probability that the data transmitted from the s-th pixel is received at the t-th response line;

$N_{tn}$ represents the normalization correction factor for the t-th response line in the n-th bed;

$R_{tn}$ represents the random correction factor for the t-th response line in the n-th bed;

$S_{tn}$ represents the scatter correction factor for the t-th response line in the n-th bed; and S' represents the set of data corresponding to the m-th subset.

At block S503, an update coefficient may be calculated based on the orthographic projection data, the set of PET projection data for the h successive beds, and the correction factors.

According to an example, the update coefficient may be calculated based on a Poisson model shown in the following formula (4):

$$C_s = \frac{1}{\sum_{n=1}^{h} \sum_{t \in Sm} A_{tn} a_{ts}} \sum_{t \in Sm} \frac{\sum_{n=1}^{h} A_{tn} N_{tn} Y_{tn} a_{ts}}{y_t} \quad (4)$$

It should be noted that, if the formula (3) is substituted into the formula (4), the formula (4) may be turned into the formula (5) below.

$$C_s = \frac{1}{\sum_{n=1}^{h} \sum_{t \in Sm} A_{tn} a_{ts}} \sum_{t \in Sm} \frac{\sum_{n=1}^{h} A_{tn} N_{tn} Y_{tn} a_{ts}}{y_t} \quad (5)$$

$$= \frac{1}{\sum_{n=1}^{h} \sum_{t \in Sm} A_{tn} a_{ts}}$$

$$\sum_{t \in Sm} \frac{\sum_{n=1}^{h} A_{tn} N_{tn} Y_{tn} a_{ts}}{\sum_{n=1}^{h} \left[ A_{tn} \left( \sum_{S'} a_{ts'} \lambda_{s'}^{(k,m)} + S_{tn} \right) \right] N_{tn} + R_{tn}}$$

Herein Cs represents the update coefficient;

$Y_{tn}$ represents the set of PET projection data for the t-th response line in the n-th bed;

$S_m$ represents a set of data corresponding to the m-th subset, and S' also represents the set of data corresponding to the m-th subset; wherein S' is embedded in $S_m$ in the formula (5), thus different symbols are adopted to show the differences between them; and $a_{ts}$ represents the probability that the data transmitted from the s-th pixel and is received at the t-th response line, and $a_{ts}'$ also represents the probability that the data transmitted from the s-th pixel is received at the t-th response line.

Be noted that, in the above formula (4) for calculating the update coefficient $C_s$, the combination $$\sum_{n=1}^{h}$$

of the PET projection data for the h successive beds is performed before calculating the ratio $$\frac{\sum_{n=1}^{h} A_{tn} N_{tn} Y_{tn} a_{ts}}{\sum_{n=1}^{h} \left[ A_{tn} \left( \sum_{S'} a_{ts'} \lambda_{s'}^{(k,m)} + S_{tn} \right) \right] N_{tn} + R_{tn}}.$$

In this way, the amount of data statistics for calculating the numerator and the denominator of the ratio may be increased, which is beneficial for reducing image noises.

In addition, those skilled in the art will understand that the update coefficient may be obtained based on other mathematical models or using other methods. For example, a least squares method may be adopted, or a method for introducing relaxation coefficient and a method for solving equations may be adopted, etc.

At block S504, the update coefficient is used for updating the current iteration reconstructed image, and the iteration number K is updated by K=K+1.

According to an example, the following formula (6) may be used for updating the image at the previous iteration:

$$\lambda_S^{(k,m+1)} = \lambda_S^{(k,m)} \cdot C_S \quad (6).$$

It should be noted that, if the formula (5) is substituted into the formula (6), the formula (6) may be turned into the formula (2) below, which is the PET image reconstruction iteration model adopted in this example.

$$\lambda_S^{(k,m+1)} = \lambda_S^{(k,m)} \cdot C_s \quad (2)$$

$$= \frac{\lambda_S^{(k,m)}}{\sum_{n=1}^{h} \sum_{t \in Sm} A_{tn} a_{ts}}$$

$$\sum_{t \in Sm} \frac{\sum_{n=1}^{h} A_{tn} N_{tn} Y_{tn} a_{ts}}{\sum_{n=1}^{h} \left[ A_{tn} \left( \sum_{S'} a_{ts'} \lambda_{s'}^{(k,m)} + S_{tn} \right) \right] N_{tn} + R_{tn}}$$

Be noted that, in the PET image reconstruction iteration model, the combination $$\sum_{n=1}^{h}$$

of the set of PET projection data for each bed of the same bed group is performed before calculating the ratio $$\frac{\sum_{n=1}^{h} A_{tn} N_{tn} Y_{tn} a_{ts}}{\sum_{n=1}^{h} \left[ A_{tn} \left( \sum_{S'} a_{ts'} \lambda_{s'}^{(k,m)} + S_{tn} \right) \right] N_{tn} + R_{tn}}.$$

In this way, the amount of data statistics for calculating the numerator and the denominator of the ratio may be increased, which is beneficial for reducing image noises.

At block S505, whether the updated iteration number K reaches a predetermined threshold is determined; in the case the updated iteration number K reaches the predetermined threshold, it represents that the PET image reconstruction is completed; and in the case the updated iteration number K is less than the predetermined threshold, return to perform the block S502.

Under normal circumstances, the predetermined iteration number may be pre-set in advance, such as three times. When the iteration number of the reconstructed PET images for the same bed group reaches the predetermined iteration number, it represents that the PET image reconstructions for the same bed group may be completed; otherwise, next iteration may be performed, thereby returning to the perform the block S502.

Be noted that, the predetermined iteration number may be an experience value. In general, the iteration number of the PET images should not be too much; otherwise, it may cause the PET images not clear and to have lots of noises.

In order to more clearly understand the method for reconstructing the PET multi-bed image provided in the above example, the following example is combined with specific scenarios for describing the above-described method for reconstructing the PET multi-bed image.

Figure 6:
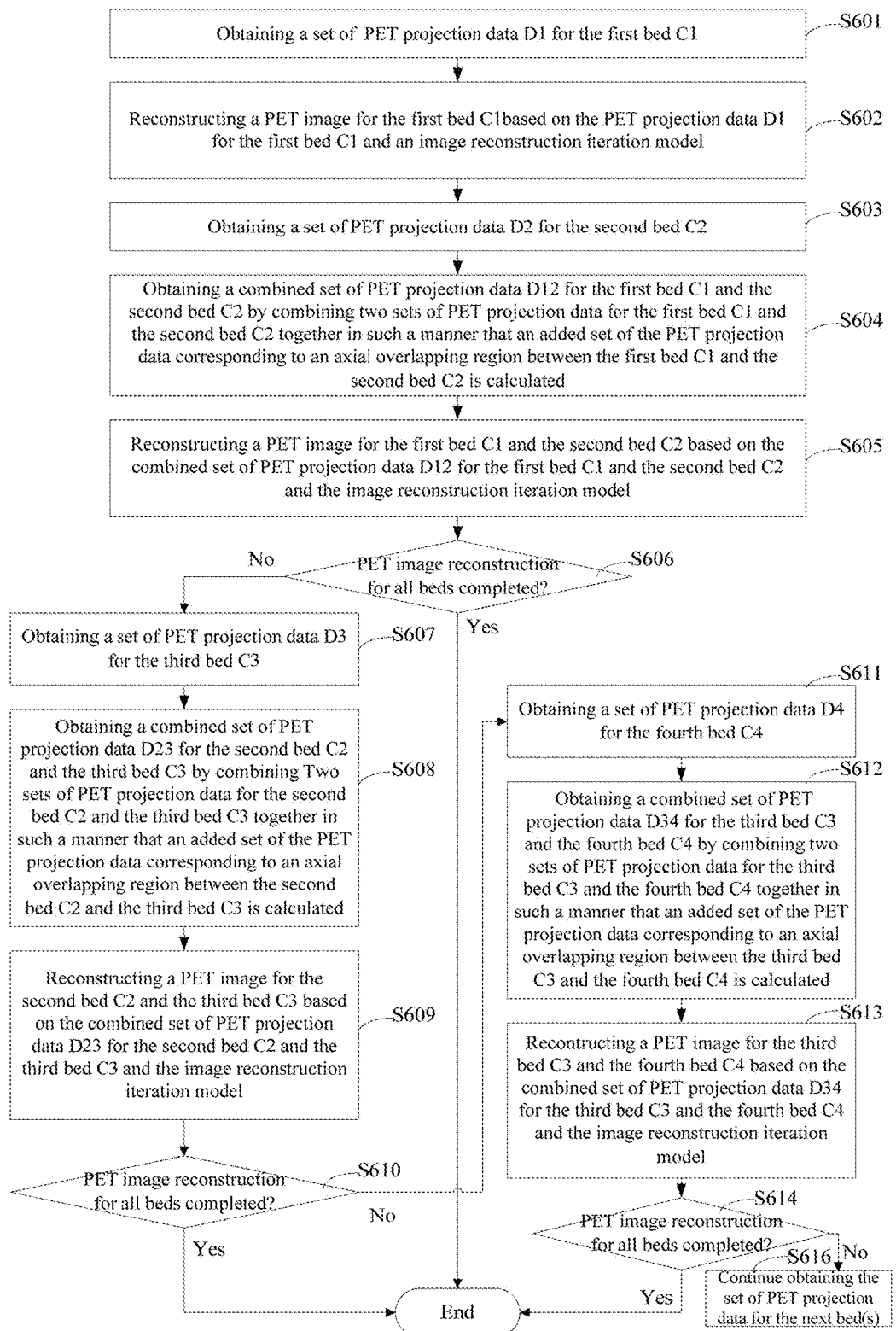
FIG. 6 is a flowchart illustrating the procedures of a method for reconstructing a PET multi-bed image according to still another example of the present disclosure.

In this example, 4 scanning beds total are set, which may be the first scanning bed C1, the second scanning bed C2, the third scanning bed C3, and the fourth scanning bed C4, respectively. Two sets of PET projection data for every two adjacent beds may be combined to perform the PET image reconstruction. Further, in this example, the PET image reconstruction iteration model shown in the above formula (2) may be adopted for performing PET image reconstruction. Referring to FIG. 6. FIG. 6 is a flowchart illustrating the procedures of a method for reconstructing a PET multi-bed image according to still another example of the present disclosure. As shown in FIG. 6, the method for reconstructing a PET multi-bed image may include the following blocks S601-S614.

At block S601, a set of PET projection data D1 for the first bed C1 may be obtained.

At block S602, a PET image for the first bed C1 may be reconstructed according to the set of PET projection data D1 for the first bed C1 and an image reconstruction iteration model.

At block S603, a set of PET projection data D2 for the second bed C2 may be obtained.

At block S604, a combined set of PET projection data D12 for the first bed C1 and the second bed C2 may be obtained by combining two sets of PET projection data for the first bed C1 and the second bed C2 together in such a manner that an added set of the PET projection data corresponding to an axial overlapping region between the first bed C1 and the second bed C2 may be calculated.

At block S605, a PET image for the first bed C1 and the second bed C2 may be reconstructed based on the combined set of PET projection data D12 for the first bed C1 and the second bed C2 and the image reconstruction iteration model.

At block S606, whether the PET image reconstruction for all beds completed may be determined. If no, go to the block S607; or if yes, the process may be ended.

At block S607, a set of PET projection data D3 for the third bed C3 may be obtained.

At block S608, a set of combined PET projection data D23 for the second bed C2 and the third bed C3 may be obtained by combining two sets of PET projection data for the second bed C2 and the third bed C3 together in such a manner that an added set of the PET projection data corresponding to an axial overlapping region between the second bed C2 and the third bed C3 may be calculated.

At block S609, a PET image for the second bed C2 and the third bed C3 may be reconstructed based on the combined set of PET projection data D23 for the second bed C2 and the third bed C3 and the image reconstruction iteration model.

At block S610, whether the PET image reconstruction for all beds completed may be determined once again. If no, go to the block S611; or if yes, the process may be ended.

At block S611, a set of PET projection data D4 for the fourth bed C4 may be obtained.

At block S612, a combined set of PET projection data D34 for the third bed C3 and the fourth bed C4 may be obtained by combining two sets of PET projection data for the third bed C3 and the fourth bed C4 together in such a manner that an added set of the PET projection data corresponding to an axial overlapping region between the third bed C3 and the fourth bed C4 may be calculated.

At block S613, a PET image for the third bed C3 and the fourth bed C4 may be reconstructed based on the combined set of PET projection data D34 for the third bed C3 and the fourth bed C4 and the image reconstruction iteration model.

At block S614, whether the PET image reconstruction for all beds completed may be determined once again. If yes, the PET image reconstruction may be ended; or if no, the method may continue to obtain the set of PET projection data for the next bed(s) at S616.

The PET image reconstruction for the four beds may be completed through the above blocks S601-S614. During the above-described PET multi-bed image reconstruction process, except that the PET image for the fourth bed C4 is reconstructed once, the PET images for the first bed C1, the second bed C2 and the third bed C3 are reconstructed twice. Therefore, in this example, it is said that the image reconstruction of seven (=1+2*(4−1)=2*4−1) beds is required.

If the above example adopts the image reconstruction iteration model shown in the above formula (1) to perform the PET image reconstruction, the set of PET projection data for all beds may need to be handled simultaneously. That is, after scanning one bed is completed, the reconstructed images for the current bed and all for the previous beds must be reconstructed. For example, 4 beds total are set. If scanning the first bed is completed at the current time, the reconstructed image for the first bed may be reconstructed; if scanning the third bed is completed at the current time, the reconstructed images for the third bed and its previous two beds may be reconstructed; and if scanning the fourth bed is completed at the current time, the reconstructed images for the fourth bed and its previous three beds will be reconstructed. Thus, the calculations during the image reconstruction process may become very large. For example, in the above example, it is said that the image reconstruction of twenty $$\left(\left[1+(1+2)+(1+2+3)+(1+2+3+4)=\frac{4\times(4+1)\times(4+2)}{6}=20\right]\right)$$

beds is required.

Assume that there are N beds during the PET scan process, wherein N≥2 and N is an integer. If the image reconstruction iteration model shown in the formula (1) is adopted for performing the PET multi-bed image reconstruction, the image reconstruction of $$1+(1+2)+(1+2+3)+(1+2+3+4)+\ldots+(1+2+3+4+\ldots+N)=$$
$$\frac{N\times(N+1)\times(N+2)}{6}$$

beds may be required. However, if the image reconstruction iteration model shown in the formula (2) is adopted for performing the PET multi-bed image reconstruction, the image reconstruction of (2*N−1) beds is required.

In order to more clearly compare advantages and disadvantages of the image reconstruction iteration models shown in the formulas (1) and (2), the following example is expressed by a tabular format, which indicates when these two image reconstruction iteration models may be adopted for performing the PET image reconstruction, the number of beds to be handled corresponding to different numbers of PET scanning beds. Please refer to Table-1.

TABLE 1

| Number of PET scanning beds | 1 | 2 | 3 | 4 | 5 | 6 | 7 | 8 |
|---|---|---|---|---|---|---|---|---|
| Number of beds to be handled when the image reconstruction iteration model shown in formula (1) is adopted for performing PET image reconstruction | 1 | 4 | 10 | 20 | 35 | 56 | 84 | 120 |

TABLE 1-continued

| Number of PET scanning beds | 1 | 2 | 3 | 4 | 5 | 6 | 7 | 8 |
|---|---|---|---|---|---|---|---|---|
| Number of beds to be handled when the image reconstruction iteration model shown in formula (2) is adopted for performing PET image reconstruction | 1 | 3 | 5 | 7 | 9 | 11 | 13 | 15 |

As can be seen, compared to the image reconstruction iteration model shown in formula (1), the number of beds to be handled may be reduced when the image reconstruction iteration model shown in formula (2) is adopted for performing the PET image reconstruction, thereby reducing calculations during the image reconstruction process.

Be noted that, in the above example, the image reconstruction may be performed after obtaining the set of PET projection data for a bed, that is to say, the image reconstruction may be performed based on the PET projection data for the bed (when the bed is the first bed C1) or a combined set of projection data for the bed and its adjacent bed. In another example, the image reconstruction may be performed after obtaining the set of PET projection data for all scanning beds.

Be noted that, in the above example, four beds are considered for describing the example. When the number of the PET scanning beds is another value, the method for reconstructing a PET multi-bed image may not limited to the blocks shown in FIG. 6, and more times or fewer times of image reconstructions may be performed based on the number of the scanning beds until image reconstructions of all beds may be completed.

Be noted that, in the above example, every two adjacent beds may be put together to perform image reconstruction for describing the example. In practice, three successive beds or four successive beds or more successive beds may be put together to perform image reconstruction. Based on the reconstructing method which using every two adjacent beds to perform image reconstruction in the above example, it is easy for those skilled in the art to think of a reconstructing method which using three successive beds or more than three successive beds to perform image reconstruction, and detailed description is omitted for brevity.

It should be noted that, for the above-described method for reconstructing a PET multi-bed image, each image reconstruction is performed based on at least two successive beds. In order to obtain a complete PET multi-bed image, the reconstructed images obtained through a plurality of image reconstruction processes may be spliced together. Therefore, a combination image for PET multi-bed image may be provided in the example of the present disclosure. Please refer to the specific example below.

Before describing the specific implementation of the example, the following settings may be set in advance. A plurality of beds may be used for PET scanning, wherein an axial overlapping region exists between every two adjacent beds among the plurality of beds; every h successive beds constitute a bed group, wherein h≥2, and h is an integer; the plurality of beds for PET scanning constitute M bed groups, wherein M≥2, and M is an integer; every two adjacent bed groups include at least one identical bed. Hereinafter, the identical bed included by every two adjacent bed groups is called "an overlapping bed".

Figure 7:
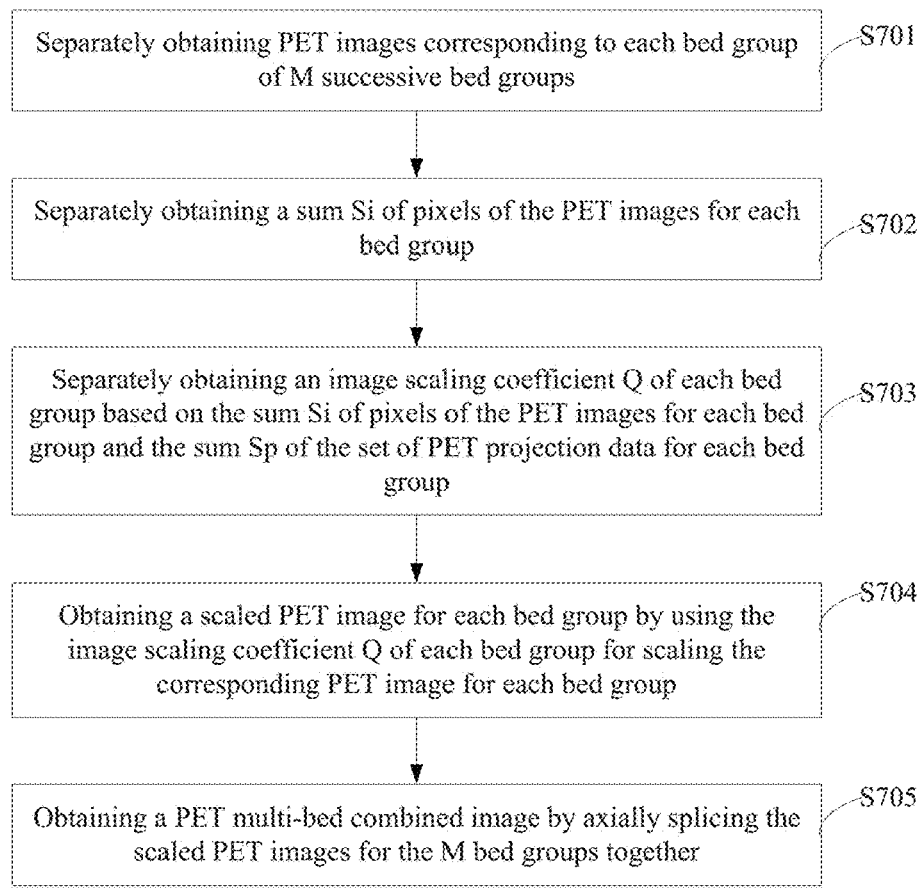
FIG. 7 is a flowchart illustrating the procedures of a method for combining a PET multi-bed image according to an example of the present disclosure.

Based on the above settings, a specific embodiment of a method for combining a PET multi-bed image is provided in the example of the present disclosure. Referring to FIG. 7.

FIG. 7 is a flowchart illustrating the procedures of a method for combining a PET multi-bed image according to an example of the present disclosure. As shown in FIG. 7, the method for combining a PET multi-bed image may include the following blocks S701-S705.

At block S701, PET images corresponding to each bed group of M successive bed groups may be separately reconstructed according to the method for reconstructing a PET multi-bed image in any one of the above-described examples.

According to an example, the block S701 may specifically include the following blocks S7011 and S7012.

At block S7011, a combined set of PET projection data for the bed group may be obtained by combining a set of PET projection data for h successive beds of each bed group together in such a manner that two sets of PET projection data corresponding to an axial overlapping region between every two adjacent beds may be added up.

This block S7011 is similar to the block S401 in the above-described example, and detailed description is omitted for brevity. Please refer to related description of the block S401.

At block S7012, a PET image for each bed group may be reconstructed based on an image reconstruction iteration model and the set of combined PET projection data for each bed group.

This block S7012 is similar to the block S402 in the above-described example, and detailed description is omitted for brevity. Please refer to related description of block S402.

At block S702, a sum Si of pixels of the PET image for each bed group may be separately calculated.

After the PET images for each bed group are reconstructed, the sum Si of pixels of the PET images for each bed group may be separately calculated, wherein the sum Si of the pixels may be a summation of all pixels of the PET images.

At block S703, an image scaling coefficient Q of each bed group may be separately calculated based on the sum Si of pixels of the PET images for each bed group and the sum Sp of the set of PET projection data for each bed group.

In this example, when calculating the sum Sp of the set of PET projection data for each bed group, a weighted summing operation may be performed on the set of PET projection data corresponding to the axial overlapping region between the h successive beds of the bed group, such that the difference between the sum of the set of PET projection data corresponding to the axial overlapping region and the sum of the set of PET projection data corresponding to the axial non-overlapping region may be as small as possible, thereby appropriately avoiding artefacts in the spliced image.

For example, a bed group may be set to include h beds, and an axial overlapping region may exist between every two adjacent beds. The set of PET projection data for each bed may be represented as follows.

The set of PET projection data for an axial overlapping region between the first bed and the second bed is represented by $Sum_{OL,12}$, and the set of PET projection data for an axial non-overlapping region of the first bed (i.e., a region that does not overlap the adjacent second bed) is represented by $Sum_{non-OL,1}$.

The set of PET projection data for an axial overlapping region between the second bed and the first bed is represented by $Sum_{OL,21}$, the set of PET projection data for an axial overlapping region between the second bed and the third bed is represented by $Sum_{OL,23}$, and the set of PET projection data for an axial non-overlapping region of the second bed (i.e., a region that does not overlap the adjacent first bed and the adjacent third bed) is represented by $Sum_{non-OL,2}$.

The set of PET projection data for an axial overlapping region between the third bed and the second bed is represented by $Sum_{OL,32}$, the set of PET projection data for an axial overlapping region between the third bed and the fourth bed is represented by $Sum_{OL,34}$, and the set of PET projection data for an axial non-overlapping region of the third bed (i.e., a region that does not overlap the adjacent second bed and the adjacent fourth bed) is represented by $Sum_{non-OL,3}$.

And so on, the set of PET projection data for an axial overlapping region between the i-th bed and the (i−1)-th bed is represented by $Sum_{OL,i(i-1)}$, the set of PET projection data for an axial overlapping region between the i-th bed and the (i+1)-th bed is represented by $Sum_{OL,i(i+1)}$, and the set of PET projection data for an axial non-overlapping region of the i-th bed (i.e., a region that does not overlap the adjacent (i−1)-th bed and the adjacent (i+1)-th bed) is represented by $Sum_{non-OL,i}$.

The set of PET projection data of an axial overlapping region between the (i+1)-th bed and the i-th bed is represented by $Sum_{OL,(i+1)i}$, the set of PET projection data for an axial overlapping region between the (i+1)-th bed and the (i+2)-th bed is represented by $Sum_{OL,(i+1)(i+2)}$, and the set of PET projection data for an axial non-overlapping region of the (i+1)-th bed (i.e., a region that does not overlap the adjacent i-th bed and the adjacent (i+2)-th bed) is represented by $Sum_{non-OL,(i+1)}$.

And so on, the set of PET projection data for an axial overlapping region between the (h−1)-th bed and the (h−2)-th bed is represented by $Sum_{OL,(h-1)(h-2)}$, the set of PET projection data for an axial overlapping region between the (h−1)-th bed and the h-th bed is represented by $Sum_{OL,(h-1)h}$, and the set of PET projection data for an axial non-overlapping region of the (h−1)-th bed (i.e., a region that does not overlap the adjacent (h−2)-th bed and the adjacent h-th bed) is represented by $Sum_{non-OL,h-1}$.

The set of PET projection data for an axial overlapping region between the h-th bed and the (h−1)-th bed is represented by $Sum_{OL,h(h-1)}$, and the set of PET projection data for an axial non-overlapping region of the h-th bed (i.e., a region that does not overlap the adjacent (h−1)-th bed) is represented by $Sum_{non-OL,h}$.

In this case, the sum Sp of the set of PET projection data for the bed group may be expressed according to the following formula (7):

$$Sp = Sum_{OL} + Sum_{non-OL} \qquad (7)$$

Herein $Sum_{non-OL}$ represents an added set of PET projection data corresponding to the axial non-overlapping region between the h beds of the bed group, which may be obtained according to the following formula (8):

$$Sum_{non-OL} = \sum_{i=1}^{h} Sum_{non-OL,i} \qquad (8)$$
$$= Sum_{non-OL,1} + Sum_{non-OL,2} + Sum_{non-OL,3} + \ldots + Sum_{non-OL,h}$$

Herein $Sum_{OL}$ represents a weighted sum of the set of PET projection data corresponding to the axial overlapping region between the h beds of the bed group, which may be obtained according to the following formula (9):

$$Sum_{OL} = \sum_{i=1}^{h-1} \omega_{i(i+1)} Sum_{OL,i(i+1)} + \omega_{(i+1)i} Sum_{OL,(i+1)i} \qquad (9)$$
$$= \omega_{12} Sum_{OL,12} + \omega_{21} Sum_{OL,21} +$$
$$\omega_{23} Sum_{OL,23} + \omega_{32} Sum_{OL,32} + \ldots +$$
$$\omega_{(h-1)h} Sum_{OL,(h-1)h} + \omega_{h(h-1)} Sum_{OL,h(h-1)}.$$

Herein $\omega_{i(i+1)}$ represents a weighting of the set of PET projection data corresponding to an axial overlapping region between the i-th bed and the (i+1)-th bed, $\omega_{(i+1)i}$ represents a weighting of the set of PET projection data corresponding to an axial overlapping region between the (i+1)-th bed and the i-th bed, wherein $\omega_{(i+1)i} + \omega_{i(i+1)}$, i∈{1, 2, 3, . . . , h−2, h−1}, and $\omega_{(i+1)i}$, $\omega_{i(i+1)}$∈(0,1). In an example, these two weightings $\omega_{i(i+1)}$ and $\omega_{(i+1)i}$ may be experience values. For example, these two weightings $\omega_{i(i+1)}$ and $\omega_{(i+1)i}$ may be 0.5, respectively.

The image scaling coefficient Q of each bed group may be equal to a ratio between the sum Sp of the set of PET projection data for the bed group and the sum Si of pixels of the PET images for the bed group. Therefore, the image scaling coefficient Q of each bed group may be obtained according to the following formula (10):

$$Q = Sp/Si \qquad (10)$$

At block S704, a scaled PET image for each bed group may be obtained by using the image scaling coefficient Q of each bed group for scaling the corresponding PET image for each bed group.

Specifically, the PET image for each bed group may be multiplied by the image scaling coefficient Q of the corresponding bed group, so as to obtain the scaled PET image for each bed group.

At block S705, a PET multi-bed combined image may be obtained by axially splicing the scaled PET images for the M bed groups together.

In an example, when the scaled PET images for the M bed groups are axially spliced together, a weighted summing operation may be performed on a corresponding portion of the scaled PET images for every two adjacent bed groups that is corresponding to a predetermined region of the overlapping bed, thereby avoiding artefacts in the spliced image (i.e., the PET multi-bed combined image). The predetermined region may be an axial non-overlapping region of the overlapping bed, that is, a region does not axially overlap any adjacent bed. In this case, the PET multi-bed combined image may be an image obtained by axially splicing a corresponding portion of the scaled PET images for each bed group that is corresponding to a non-overlapping bed (also called "a non-overlapping portion of the scaled PET images for each bed group") and the overlapping image for every two adjacent bed groups together. In an example, the overlapping image for every two adjacent bed groups may be obtained by performing a weighted summing operation on a corresponding portion of the scaled PET images for every two adjacent bed groups that is corresponding to the predetermined region of the overlapping bed.

Figure 8:
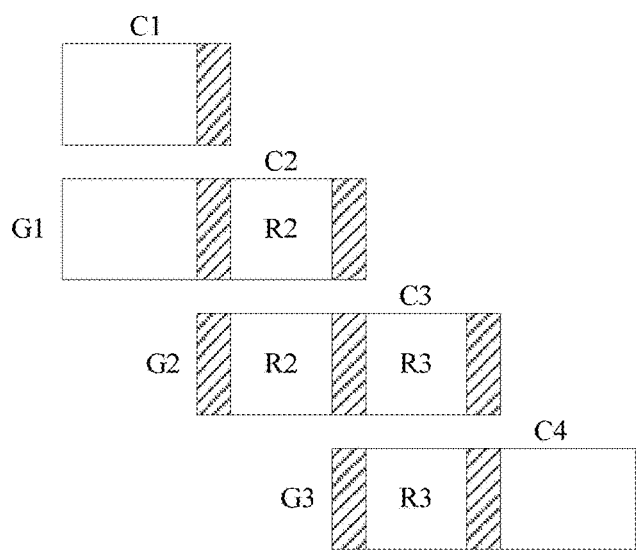
FIG. 8 is a schematic diagram showing regions of an overlapping bed between adjacent bed groups.

In the following, a predetermined region of the overlapping bed of every two adjacent beds is introduced in conjunction with the figures. Referring to FIG. 8. FIG. 8 is a schematic diagram showing regions of an overlapping bed between adjacent bed groups. In FIG. 8, symbols C1, C2, C3, and C4 are used for representing a first bed, a second bed, a third bed, and a fourth bed, respectively; symbols G1, G2, and G3 are used for representing a first bed group, a second bed group, and a third bed group. In FIG. 8, a shaded region is used for representing an axial overlapping region between adjacent beds, and a blank region is used for representing an axial non-overlapping region of each bed. The first bed C1 and the second bed C2 constitute the first bed group G1, the second bed C2 and the third bed C3 constitute the second bed group G2, and the third bed C3 and the fourth bed C4 constitute the third bed group G3.

The second bed C2 is the overlapping bed of the first bed group G1 and the second bed group G2, and the predetermined region of the overlapping bed is an axial non-overlapping region of the second bed C2, that is, the blank region R2 shown in FIG. 8. Similarly, the third bed C3 is the overlapping bed of the second bed group G2 and the third bed group G3, and the predetermined region of the overlapping bed is an axial non-overlapping region of the third bed C3, that is, the blank region R3 shown in FIG. 8.

The predetermined region of the overlapping bed of every two adjacent bed groups may include a plurality of layers as shown in FIG. 3. In this case, when performing a weighted summing operation on a corresponding portion of the scaled PET images for every two adjacent bed groups that is corresponding to the predetermined region of the overlapping bed, weightings of a corresponding portion of the scaled PET images for the pervious bed group that is corresponding to the plurality of layers of the predetermined region of the overlapping bed may be set to be decreased or unchanged with an increasing layer number, and weightings of a corresponding portion of the scaled PET images for the next bed group that is corresponding to the plurality of layers of the predetermined region of the overlapping bed may be set to be increased or unchanged with the increasing layer number. For example, in FIG. 8, when a weighted summing operation is performed on a corresponding portion of the scaled PET images for the first bed group G1 and the second bed group G2 that is corresponding to the predetermined region R2 of the overlapping bed C2, the weightings of a corresponding portion of the scaled PET images for the first bed group G1 that is corresponding to the plurality of layers of the predetermined region R2 of the overlapping bed C2 may be set to be decreased or unchanged with an increasing layer number, and the weightings of a corresponding portion of the scaled PET images for the second bed group G2 that is corresponding to the plurality of layers of the predetermined region R2 of the overlapping bed C2 may be set to be increased or unchanged with the increasing layer number. As can be seen from the relationship between an axial sensitivity and layers when collecting data by a PET scan shown in FIG. 2, noise levels on these final few layers of the PET image for the previous bed group will be increased with the increasing layer number, but noise levels on these first few layers of the PET image for the next bed group will be decreased with the increasing layer number. Through providing larger weightings to the images having lower noise levels, the whole noise level of the combined image may be appropriately controlled. In another example, those skilled in the art should appreciate that many methods may be used for determining the weightings during the process of performing the weighted summing operation. For example, a layer position of the image and/or a noise level of the image may be used for determining the weightings.

The above is a specific embodiment of the method for combining a PET multi-bed image provided in the example of the present disclosure. When calculating the sum Sp of the set of PET projection data for each bed group, a weighted summing operation may be performed on the set of PET projection data corresponding to the axial overlapping region between every two adjacent beds of every bed group, such that the sum Sp of the set of PET projection data for each bed group may be proportional to the sum Si of pixels of the PET image for the corresponding bed group. Therefore, it ensures that the scaled images for the overlapping regions between the adjacent beds may be at the same range, thereby avoiding artefacts in the spliced image to be beneficial for improving signal-to-noise ratio of the spliced image.

Figure 9A:
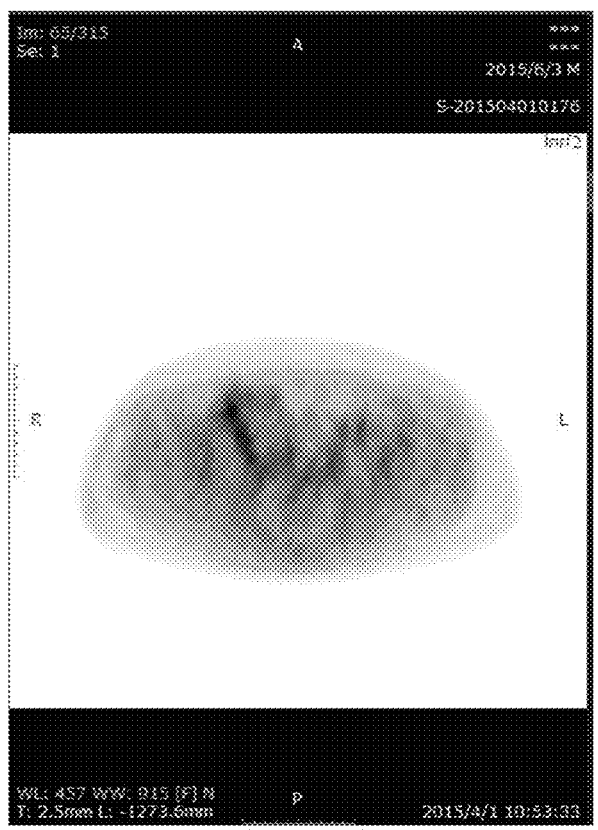
FIG. 9A is a schematic diagram of a PET image outputted by using the combining method in an example of the present disclosure.
Figure 9B:
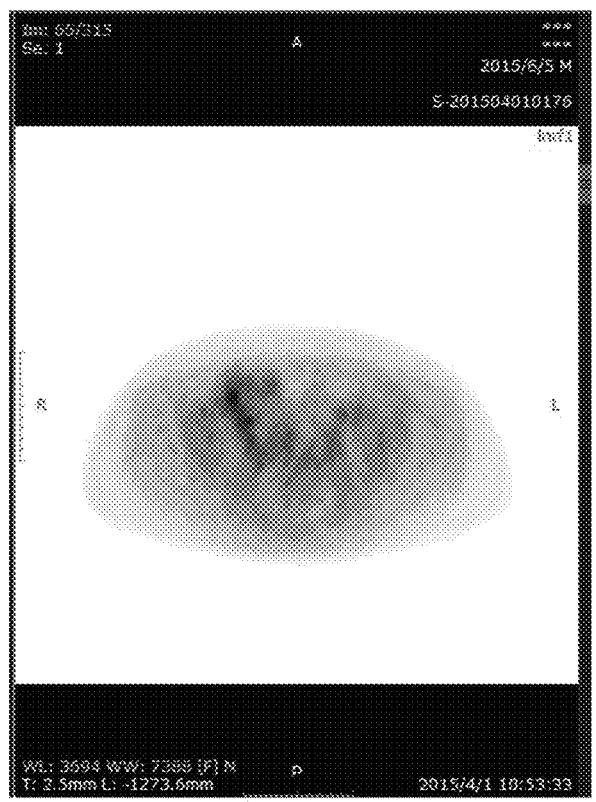
FIG. 9B is a schematic diagram of a PET image outputted by using an image-based combining method.

Referring to FIG. 9A and FIG. 9B. FIG. 9A is a schematic diagram of a PET image outputted by using the combining method in the example of the present disclosure, and FIG. 9B is a schematic diagram of a PET image outputted by using an image-based combining method. As can be seen from FIG. 9A and FIG. 9B, the PET image outputted by using the combining method in the example of the present disclosure has a lower noise level.

Be noted that, a conventional image-based combining method may be described as follows. For overlapping regions physically between adjacent beds, x and y are respectively two overlapping region images of a single bed image to be combined, and z is the combined image. The combined image z may be expressed according to the following formula (11):

$$z = \omega_x x + \omega_y y \tag{11}$$

Herein, $\omega_x = \dfrac{1}{1+\dfrac{\sigma_x^2}{\sigma_y^2}}$, $\omega_x = \dfrac{1}{1+\dfrac{\sigma_y^2}{\sigma_x^2}}$, and $\sigma_i \propto \dfrac{CV_i}{NEC_i}$;

$\omega x$ represents a weighting of the image x, and $\omega y$ represents weighting of the image y, wherein $0<\omega_x, w_y<1$;

CVi is a variance of the i-th bed image; and

NECi is a noise equal count of the i-th bed image, which is a technical term in the PET field, and may be approximately understood as a signal-to-noise ratio.

As can be seen, in the prior art, during the image combination process, the regions for splicing images respectively correspond to an edge region of single bed scanning, wherein this region has a lower signal-to-noise ratio. In the example of the present disclosure, the regions for splicing images correspond to a center region of single bed scanning, wherein this region has a higher signal-to-noise ratio. Therefore, compared to the image combination method in the prior art, the image combination method in the example of the present disclosure may avoid noise overlapping, which is beneficial for improving signal-to-noise ratio of the images.

Figure 10:
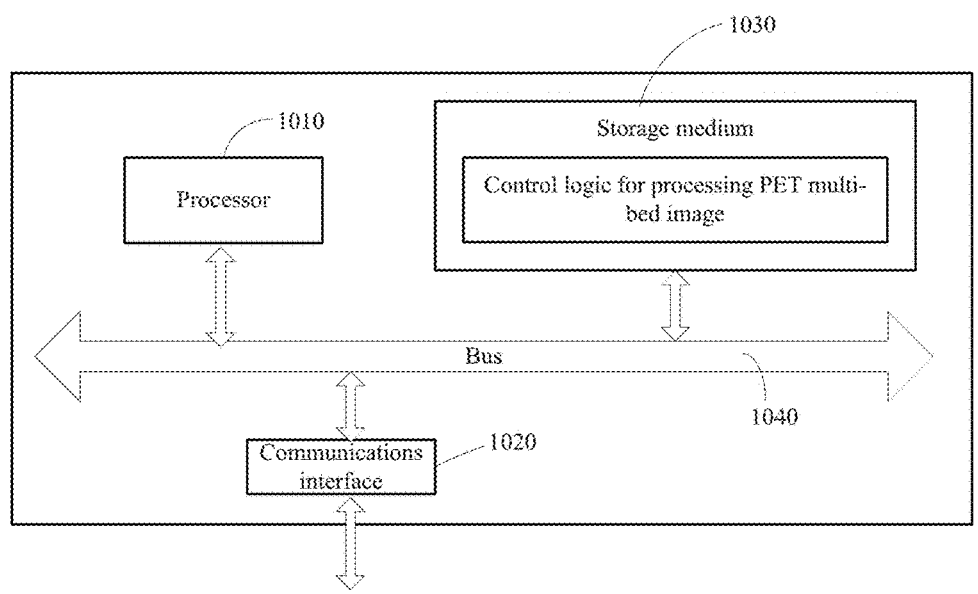
FIG. 10 is a hardware architecture diagram of a control device for processing a PET multi-bed image according to an example of the present disclosure.

The reconstructing method and combining method for the PET multi-bed image in the above-described examples may be performed by a control device shown in FIG. 10. Referring to FIG. 10. FIG. 10 is a hardware architecture diagram of a control device for processing a PET multi-bed image according to an example of the present disclosure. The control device shown in FIG. 10 may include a processor 1010, a communications interface 1020, a machine readable storage medium 1030, and a bus 1040, wherein the processor 1010, the communications interface 1020, and the machine readable storage medium 1030 may be communicated to each other through the bus 1040.

In an example, the machine readable storage medium 1030 may be used for storing machine readable instructions corresponding to a control logic for processing a PET multi-bed image, wherein the machine readable storage medium 1030 may be a non-volatile memory. The processor 1010 may invoke machine readable instructions corresponding to a control logic for processing a PET multi-bed image and execute the machine readable instructions to execute the above-described reconstructing and/or combining method for a PET multi-bed image. For example, the machine readable instructions corresponding to a control logic for processing a PET multi-bed image may be programs corresponding to control software. When the processor 1010 executes the machine readable instructions, the control device may accordingly display a function interface corresponding to the machine readable instructions on a display screen.

When the function of the machine readable instructions corresponding to a control logic for processing a PET multi-bed image may be implemented by a software function module and is used as a standalone product for sale or for use, it may be stored in a computer readable storage medium. Based on such understanding, a technical scheme of the present disclosure or a part of said technical scheme contributed to the prior art or a part of said technical scheme may be embodied in the form of a software product, and the computer software product may be stored in a storage medium, which may include several instructions for instructing a computer device (such as, a personal computer, a server, or a network equipment, etc.) to execute all or a part of the blocks of the methods in various examples of the present disclosure. The above-described storage medium may include: USB Flash Drive, Removable Hard Disk, Read-Only Memory (ROM), Random Access Memory (RAM), Floppy Disk, or CD-ROM, or similar storage medium capable of storing program codes, or a combination thereof.

The above-described control logic for processing a PET multi-bed image may be divided into a plurality of functional modules according to functions of the device. Please refer to the following example for specific implementations.

Figure 11:
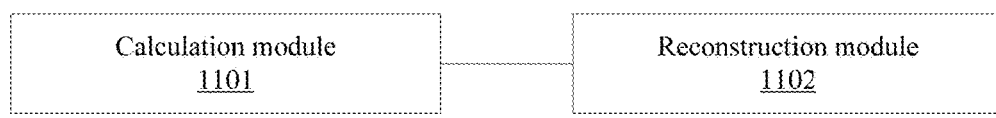
FIG. 11 is a block diagram showing function modules of a control logic for processing a PET multi-bed image according to an example of the present disclosure.

The above-described control logic for processing a PET multi-bed image may be used for reconstructing the PET multi-bed image. Be noted that, the PET multi-bed image reconstruction may be applied to the following condition: an axial overlapping region exists between every two adjacent beds. Referring to FIG. 11. FIG. 11 is a block diagram showing function modules of a control logic for processing a PET multi-bed image according to an example of the present disclosure. As shown in FIG. 11, the control logic may include a calculation module 1101 and a reconstruction module 1102.

The calculation module 1101 may be used for obtaining a combined set of PET projection data for the plurality of beds by combining a set of PET projection data for a plurality of successive beds together in such a manner that two sets of PET projection data corresponding to an axial overlapping region between every two adjacent beds may be added up.

The reconstruction module 1102 may be used for reconstructing a PET image for the at least two beds based on an image reconstruction iteration model and the combined set of PET projection data for the at least two beds.

According to an example, the reconstruction module 1102 may adopt the image reconstruction iteration model shown in the following formula:

$$\lambda_S^{(k,m+1)} = \frac{\lambda_S^{(k,m)}}{\sum_{n=1}^{h}\sum_{t\in Sm} A_{tn}a_{ts}} \sum_{t\in Sm} \frac{\sum_{n=1}^{h} A_{tn}N_{tn}Y_{tn}a_{ts}}{\sum_{n=1}^{h}\left[A_{tn}\left(\sum_{S'} a_{ts}, \lambda_{S'}^{(k,m)} + S_{tn}\right)\right]N_{tn} + R_{tn}}.$$

Herein λ represents the reconstructed PET image, k represents an iteration number, and m represents a serial number of a subset;

h represents the number of beds corresponding to the combined set of PET projection data, h≥2, and h is an integer; n represents a serial number of a bed, n∈{1, 2, 3, . . . ,h}, and n is an integer;

Atn represents an attenuation correction factor for a t-th response line in an n-th bed;

ats represents the probability that the data transmitted from the s-th pixel is received at the t-th response line;

ats' also represents the probability that the data transmitted from the s-th pixel is received at the t-th response line;

Ytn represents the set of PET projection data for the t-th response line in the n-th bed;

Ntn represents a normalization correction factor for the t-th response line in the n-th bed;

Rtn represents a random correction factor for the t-th response line in the n-th bed;

Stn represents a scatter correction factor for the t-th response line in the n-th bed; and Sm represents a set of data corresponding to the m-th subset, and S' also represents a set of data corresponding to the m-th subset.

The above-described control logic for processing a PET multi-bed image may be used for combining the PET multi-bed image. Be noted that, the PET multi-bed image combination may be applied to the following condition: for a plurality of beds for PET scanning, an axial overlapping region exists between every two adjacent beds; every h successive beds may constitute a bed group, h≥2, and h is an integer; the plurality of beds for PET scanning may constitute M bed groups, M≥2, and M is an integer; every two adjacent bed groups may include at least the same bed, hereinafter the same bed included by every two adjacent bed group may be called an overlapping bed.

Figure 12:
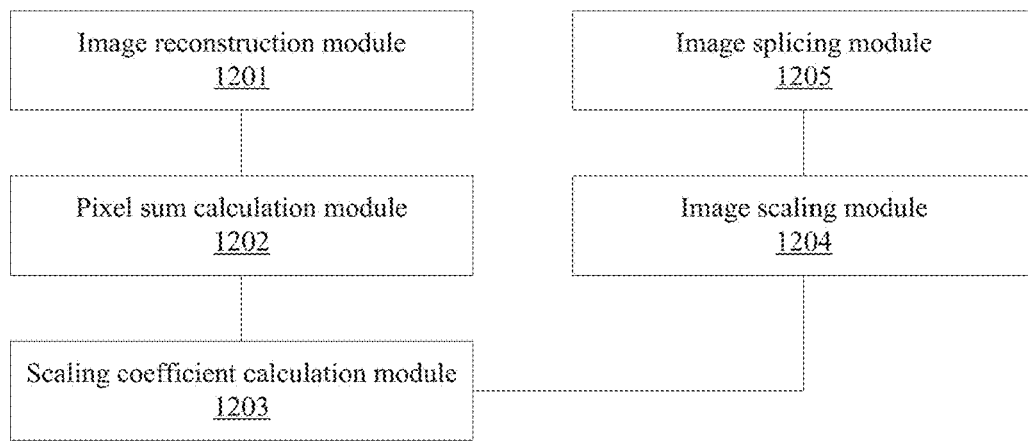
FIG. 12 is a block diagram showing function modules of a control logic for processing a PET multi-bed image according to another example of the present disclosure.

Referring to FIG. 12. FIG. 12 is a block diagram showing function modules of a control logic for processing a PET multi-bed image according to another example of the present disclosure. As shown in FIG. 12, the control logic may include an image reconstruction module 1201, a pixel sum calculation module 1202, a scaling coefficient calculation module 1203, an image scaling module 1204, and an image splicing module 1205.

The image reconstruction module 1201 may be used for separately reconstructing PET images for each bed group of the M successive bed groups according to the reconstruction methods in any one of the above-described examples.

The pixel sum calculation module 1202 may be used for separately calculating a sum Si of pixels of the PET images for each bed group.

The scaling coefficient calculation module 1203 may be used for separately calculating an image scaling coefficient Q of each bed group based on the sum Si of pixels of the PET images for each bed group and the sum Sp of the set of PET projection data for each bed group; wherein the sum Sp of the set of PET projection data for each bed group may equal to a total summation of an added set of PET projection data corresponding to the axial non-overlapping regions between the h beds of the bed group and a weighted sum of a set of PET projection data corresponding to the axial overlapping regions between the h beds of the bed group.

The image scaling module 1204 may be used for obtaining a scaled PET image for each bed group by using the image scaling coefficient Q of each bed group for scaling the corresponding PET image for each bed group.

The image splicing module 1205 may be used for obtaining a PET multi-bed combined image by axially splicing the scaled PET images for the M bed groups together.

In another example, the image splicing module 1205 may further include a weighted summing sub-module and an image splicing sub-module. The weighted summing sub-module may be used for obtaining an overlapping image for every two adjacent bed groups by performing a weighted summing operation on a corresponding portion of the scaled PET images for every two adjacent bed groups that is corresponding to the predetermined region of the overlapping bed. The image splicing sub-module may be used for obtaining the PET multi-bed combined image by axially splicing a corresponding portion of the scaled PET images for the M bed groups that is corresponding to the non-overlapping bed and the overlapping image for every two adjacent bed groups together. The predetermined region between the overlapping bed may be a region between the overlapping bed that does not axially overlap adjacent beds.

In another example, the predetermined region between the overlapping bed of every two adjacent bed groups may include a plurality of layers as shown in FIG. 3. In this case, when performing a weighted summing operation on a corresponding portion of the scaled PET images for every two adjacent bed groups that is corresponding to the predetermined region of the overlapping bed, weightings of a corresponding portion of the scaled PET images for the pervious bed group that is corresponding to the plurality of layers of the predetermined region between the overlapping bed may be set to be decreased or unchanged with an increasing layer number, and weightings of a corresponding portion of the scaled PET images for the next bed group that is corresponding to the plurality of layers of the predetermined region between the overlapping bed may be set to be increased or unchanged with the increasing layer number. As can be seen from the relationship between an axial sensitivity and layers when collecting data by a PET scan shown in FIG. 2, noise levels on these final few layers of the PET image for the previous bed group will be increased with the increasing layer number, but noise levels on these first few layers of the PET image for the next bed group will be decreased with the increasing layer number. Through providing larger weightings to the images having lower noise levels, the whole noise level of the combined image may be appropriately controlled. In another example, those skilled in the art should appreciate that many methods may be used for determining the weightings during the process of performing the weighted summing operation. For example, a layer position of the image and/or a noise level of the image may be used for determining the weightings.

The above are only preferred examples of the present disclosure is not intended to limit the disclosure within the spirit and principles of the present disclosure, any changes made, equivalent replacement, or improvement in the protection of the present disclosure should contain within the range.

The methods, processes and units described herein may be implemented by hardware (including hardware logic circuitry), software or firmware or a combination thereof. The term 'processor' is to be interpreted broadly to include a processing unit, ASIC, logic unit, or programmable gate array etc. The processes, methods and functional units may all be performed by the one or more processors; reference in this disclosure or the claims to a 'processor' should thus be interpreted to mean 'one or more processors'.

Further, the processes, methods and functional units described in this disclosure may be implemented in the form of a computer software product. The computer software product is stored in a storage medium and comprises a plurality of instructions for making a processor to implement the methods recited in the examples of the present disclosure.

The figures are only illustrations of an example, wherein the units or procedure shown in the figures are not necessarily essential for implementing the present disclosure. Those skilled in the art will understand that the units in the device in the example can be arranged in the device in the examples as described, or can be alternatively located in one or more devices different from that in the examples. The units in the examples described can be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method for reconstructing a Positron Emission Tomography (PET) multi-bed image, the method comprising:
   obtaining a set of PET projection data corresponding to each of a plurality of beds successive in an axial direction, wherein an axial overlapping region exists between every two adjacent beds among the plurality of beds;
   constructing M bed groups from the plurality of beds such that each of the M bed groups comprises h beds successive in the axial direction and at least one overlapping bed exists between every two adjacent bed groups, wherein M is an integer no less than 2 and h is an integer no less than 2; and
   for each of the M bed groups,
      obtaining an added set of PET projection data corresponding to the axial overlapping region between every two adjacent beds in the bed group by directly adding up two sets of PET projection data corresponding to the axial overlapping region between the two adjacent beds;
      obtaining a combined set of PET projection data for the bed group, with a weighted summing operation, by axially splicing a set of PET projection data corresponding to an axial non-overlapping region between each of the h beds in the bed group and the added set of PET projection data corresponding to the axial overlapping region between every two adjacent beds in the bed group together;

reconstructing a PET image for the bed group based on an image reconstruction iteration model and the combined set of PET projection data for the bed group;

obtaining a sum of pixels of the PET image for the bed group;

obtaining an image scaling coefficient for the bed group based on the sum of pixels of the PET image and the combined set of the PET projection data for the bed group;

obtaining a scaled PET image for the bed group with the image scaling coefficient for scaling the PET image for the bed group;

obtaining a PET multi-bed combined image by axially splicing the scaled PET images for the M bed groups together; and displaying the reconstructed PET image for the bed group via a display screen.

2. The method according to claim 1, wherein said image reconstruction iteration model is as follows:

$$\lambda_s^{(k,m+1)} = \frac{\lambda_s^{(k,m)}}{\sum_{n=1}^{h} \sum_{t \in Sm} A_{tn} a_{ts}} \sum_{t \in Sm} \frac{\sum_{n=1}^{h} A_{tn} N_{tn} Y_{tn} a_{ts}}{\sum_{n=1}^{h} \left[ A_{tn} \left( \sum_{S'} a_{ts} \cdot \lambda_{s'}^{(k,m)} + S_{tn} \right) \right] N_{tn} + R_{tn}};$$

wherein λ represents the PET image, k represents an iteration number, and m represents a serial number of a subset;

h represents a number of beds corresponding to the combined set of PET projection data, h≥2, and h is an integer; n represents a serial number of a bed, n∈{1, 2, 3, . . . , h}, and n is an integer;

$A_{tn}$ represents an attenuation correction factor for a t-th response line in an n-th bed;

$a_{ts}$ represents a probability that data transmitted from the s-th pixel is received at the t-th response line;

$a_{ts}'$ also represents the probability that the data transmitted from the s-th pixel is received at the t-th response line;

$Y_{tn}$ represents a set of PET projection data for the t-th response line in the n-th bed;

$N_{tn}$ represents a normalization correction factor for the t-th response line in the n-th bed;

$R_{tn}$ represents a random correction factor for the t-th response line in the n-th bed;

$S_{tn}$ represents a scatter correction factor for the t-th response line in the n-th bed; and $S_m$ represents a set of data corresponding to an m-th subset, and S' also represents the set of data corresponding to the m-th subset.

3. The method according to claim 2, wherein said reconstructing the PET image for the bed group based on the image reconstruction iteration model and the combined set of PET projection data for the bed group comprises:

obtaining an initial image, the combined set of PET projection data for the bed group and one or more of the correction factors, and setting the iteration number to 0;

obtaining a set of orthographic projection data by performing an orthographic projection based on a current iteration reconstructed image, the combined set of PET projection data for the bed group and one or more of the correction factors, wherein the current iteration reconstructed image at a first iteration is the initial image;

obtaining an updated coefficient based on the set of orthographic projection data, the combined set of PET projection data for the bed group and one or more of the correction factors;

obtaining a new iteration reconstructed image by updating the current iteration reconstructed image with the updated coefficient and adding 1 to the iteration number; and re-obtaining a new set of orthographic projection data and a new updated coefficient in a case the iteration number is less than a predetermined threshold, so as to continue iteration.

4. The method according to claim 3, wherein the set of orthographic projection data is obtained according to the following formula:

$$y_t = \sum_{n=1}^{h} \left[ A_{tn} \left( \sum_{S'} a_{ts} \cdot \lambda_{s'}^{(k,m)} + S_{tn} \right) \right] N_{tn} + R_{tn};$$

wherein $y_t$ represents the set of orthographic projection data;

λ represents the iteration reconstructed image, k represents the iteration number, and m represents a serial number of a subset;

h represents the number of the beds corresponding to the combined set of PET projection data; h≥2, and h is an integer; n represents the serial number of a bed, n∈{1, 2, 3, . . . , h}, and n is an integer;

$A_{tn}$ represents the attenuation correction factor of the t-th response line in the n-th bed;

$a_{ts}'$ represents the probability that the data transmitted from the s-th pixel is received at the t-th response line;

$N_{tn}$ represents the normalization correction factor for the t-th response line in the n-th bed;

$R_{tn}$ represents the random correction factor for the t-th response line in the n-th bed;

$S_{tn}$ represents the scatter correction factor for the t-th response line in the n-th bed; and S' represents the set of data corresponding to the m-th subset.

5. The method according to claim 3, wherein said updated coefficient is calculated according to the following formula:

$$C_s = \frac{1}{\sum_{n=1}^{h} \sum_{t \in Sm} A_{tn} a_{ts}} \sum_{t \in Sm} \frac{\sum_{n=1}^{h} A_{tn} N_{tn} Y_{tn} a_{ts}}{y_t};$$

wherein $C_s$ represents the updated coefficient;

$A_{tn}$ represents the attenuation correction factor for the t-th response line in the n-th bed;

$a_{ts}$ represents the probability that the data transmitted from the s-th pixel is received at the t-th response line;

$S_m$ represents the set of data corresponding to the m-th subset;

$N_{tn}$ represents the normalization correction factor for the t-th response line in the n-th bed;

$Y_{tn}$ represents the set of PET projection data for the t-th response line in the n-th bed; and $y_t$ represents the set of orthographic projection data.

6. The method according to claim 1, wherein the combined set of PET projection data for the bed group is calculated according to the following formula:

$$Sp = \sum_{i=1}^{h} Sum_{non-OL,i} + \sum_{i=1}^{h-1} \omega_{i(i+1)} Sum_{OL,i(i+1)} + \omega_{(i+1)i} Sum_{OL,(i+1)i};$$

wherein Sp represents the combined set of PET projection data for the bed group;

$Sum_{non-OL,i}$ represents a set of PET projection data corresponding to an axial non-overlapping region between the i-th bed of the bed group;

$Sum_{OL,i(i+1)}$ represents two sets of PET projection data corresponding to an axial overlapping region between the i-th bed and the (i+1)-th bed of the bed group;

$Sum_{OL,i(i+1)i}$ represents two sets of PET projection data corresponding to an axial overlapping region between the (i+1)-th bed and the i-th bed of the bed group; and $\omega_{i(i+1)}$ represents a weighting of $Sum_{OL,i(i+1)}$, $\omega_{(i+1)i}$ represents a weighting of $Sum_{OL,i(i+1)i}$, wherein $\omega_{(i+1)i} + \omega_{i(i+1)} = 1$, and $\omega_{(i+1)i}, \omega_{i(i+1)} \in (0,1)$.

7. The method according to claim 1, wherein obtaining the PET multi-bed combined image by axially splicing the scaled PET images for the M bed groups together, comprises:

obtaining an overlapping image for every two adjacent bed groups by performing a second weighted summing operation on a corresponding portion of the scaled PET images for every two adjacent bed groups that is corresponding to the axial non-overlapping region between the overlapping beds; and obtaining the PET multi-bed combined image by axially splicing a corresponding portion of the scaled PET images for the M bed groups that is corresponding to the non-overlapping beds and the overlapping image for every two adjacent bed groups together.

8. The method according to claim 7, wherein, if the axial non-overlapping region between the overlapping beds includes a plurality of layers, weightings of the second weighted summing operation is determined by the following:

setting the weightings of a corresponding portion of the scaled PET images for axially-forward bed groups that is corresponding to the plurality of layers of the axial non-overlapping region of the overlapping beds to be decreased or unchanged with an increasing layer number; and setting the weightings of a corresponding portion of the scaled PET images for axially-rearward bed groups that is corresponding to the plurality of layers of the axial non-overlapping region of the overlapping beds to be increased or unchanged with the increasing layer number.

9. A processing PET multi-bed image device, the device comprising:

a processor which invokes machine readable instructions corresponding to a control logic for PET multi-bed image processing stored on a storage medium and executes the machine readable instructions to:

obtain a set of PET projection data corresponding to each of a plurality of beds successive in an axial direction, wherein an axial overlapping region exists between every two adjacent beds among the plurality of beds;

construct M bed groups from the plurality of beds such that each of the M bed groups comprises h beds successive in the axial direction and at least one overlapping bed exists between every two adjacent bed groups, wherein M is an integer no less than 2 and h is an integer no less than 2;

for each of the M bed groups,
obtain an added set of PET projection data corresponding to the axial overlapping region between every two adjacent beds in the bed group by directly adding up two sets of PET projection data corresponding to the axial overlapping region between the two adjacent beds;

obtain a combined set of PET projection data for the bed group, with a weighted summing operation, by axially splicing a set of PET projection data corresponding to an axial non-overlapping region between each of the h beds in the bed group and the added set of PET projection data corresponding to the axial overlapping region between every two adjacent beds in the bed group together;

reconstruct a PET image for the bed group based on an image reconstruction iteration model and the combined set of PET projection data for the bed group;

obtain a sum of pixels of the PET image for the bed group;

obtain an image scaling coefficient for the bed group based on the sum of pixels of the PET image and the combined set of the PET projection data for the bed group;

obtain a scaled PET image for the bed group with the image scaling coefficient for scaling the PET image for the bed group; and obtain a PET multi-bed combined image by axially splicing the scaled PET images for the M bed groups together.

10. The device according to claim 9, wherein said image reconstruction iteration model is as follows:

$$\lambda_S^{(k,m+1)} = \frac{\lambda_S^{(k,m)}}{\sum_{n=1}^{h} \sum_{t \in Sm} A_{tn} a_{ts}} \sum_{t \in Sm} \frac{\sum_{n=1}^{h} A_{tn} N_{tn} Y_{tn} a_{ts}}{\sum_{n=1}^{h} \left[ A_{tn} \left( \sum_{S'} a_{ts'} \lambda_{S'}^{(k,m)} + S_{tn} \right) \right] N_{tn} + R_{tn}};$$

wherein $\lambda$ represents a reconstructed PET image, k represents an iteration number, and m represents a serial number of a subset;

h represents a number of beds corresponding to the combined set of PET projection data; h≥2, and h is an integer; n represents a serial number of a bed, n∈{1, 2, 3, ..., h}, and n is an integer;

$A_{tn}$ represents an attenuation correction factor for a t-th response line in an n-th bed;

$a_{ts}$ represents a probability that the data transmitted from an s-th pixel is received at the t-th response line;

$a_{ts}'$ also represents the probability that the data transmitted from the s-th pixel is received at the t-th response line;

$Y_{tn}$ represents a set of PET projection data for the t-th response line in the n-th bed;

$N_{tn}$ represents a normalization correction factor for the t-th response line in the n-th bed;

$R_{tn}$ represents a random correction factor for the t-th response line in the n-th bed;

$S_{tn}$ represents a scatter correction factor for the t-th response line in the n-th bed; and $S_m$ represents a set of data corresponding to the m-th subset, and S' also represents the set of data corresponding to the m-th subset.

11. The device according to claim 10, wherein, for reconstructing the PET image for the bed group based on the image reconstruction iteration model and the combined set of PET projection data for the bed group, said machine readable instructions further cause the processor to:

obtain an initial image, the combined set of PET projection data for the bed group and one or more of the correction factors, and set the iteration number to 0;

obtain a set of orthographic projection data by performing an orthographic projection based on a current iteration reconstructed image, the combined set of PET projection data for the bed group, and one or more of the correction factors, wherein a current iteration reconstructed image at a first iteration is the initial image;

obtain an updated coefficient based on the set of orthographic projection data, the combined set of PET projection data for the bed group, and one or more of the correction factors;

obtain a new iteration reconstructed image by updating the current iteration reconstructed image with the updated coefficient, and add 1 to the iteration number; and re-obtain a new set of orthographic projection data and a new updated coefficient in a case the iteration number is less than a predetermined threshold, so as to continue iteration.

12. The device according to claim 11, wherein the set of orthographic projection data is obtained according to the following formula:

$$y_t = \sum_{n=1}^{h} \left[ A_{tn}\left(\sum_{s'} a_{ts}, \lambda_{s'}^{(k,m)} + S_{tn}\right) \right] N_{tn} + R_{tn};$$

wherein $y_t$ represents the set of orthographic projection data;

$\lambda$ represents the iteration reconstructed image, k represents the iteration number, and m represents a serial number of a subset;

h represents the number of beds corresponding to the combined set of PET projection data; h≥2, and h is an integer; n represents the serial number of a bed, n∈{1, 2, 3, . . . , h}, and n is an integer;

$A_{tn}$ represents the attenuation correction factor for the t-th response line in the n-th bed;

$a_{ts}'$ represents the probability that the data transmitted from the s-th pixel is received at the t-th response line;

$N_{tn}$ represents the normalization correction factor for the t-th response line in the n-th bed;

$R_{tn}$ represents the random correction factor for the t-th response line in the n-th bed;

$S_{tn}$ represents the scatter correction factor for the t-th response line in the n-th bed; and S' represents the set of data corresponding to the m-th subset.

13. The device according to claim 11, wherein the updated coefficient is calculated according to the following formula:

$$C_s = \frac{1}{\sum_{n=1}^{h}\sum_{t \in Sm} A_{tn}a_{ts}} \sum_{t \in Sm} \frac{\sum_{n=1}^{h} A_{tn}N_{tn}Y_{tn}a_{ts}}{y_t};$$

wherein $C_s$ represents the updated coefficient;

$A_{tn}$ represents the attenuation correction factor for the t-th response line in the n-th bed;

$a_{ts}$ represents the probability that the data transmitted from the s-th pixel is received at the t-th response line;

$S_m$ represents the set of data corresponding to the m-th subset;

$N_{tn}$ represents the normalization correction factor for the t-th response line in the n-th bed;

$Y_{tn}$ represents the set of PET projection data for the t-th response line in the n-th bed; and $y_t$ represents the set of orthographic projection data.

14. The device according to claim 9, wherein said machine readable instructions further cause the processor to obtain the combined set of PET projection data for the bed group according to the following formula:

$$Sp = \sum_{i=1}^{h} Sum_{non-OL,i} + \sum_{i=1}^{h-1} \omega_{i(i+1)}Sum_{OL,i(i+1)} + \omega_{(i+1)i}Sum_{OL,(i+1)i};$$

wherein Sp represents the combined set of PET projection data for the bed group;

$Sum_{non-OL,i}$ represents a set of PET projection data corresponding to an axial non-overlapping region between the i-th bed of the bed group;

$Sum_{OL,i(i+1)}$ represents two sets of PET projection data corresponding to an axial overlapping region between the i-th bed and the (i+1)-th bed of the bed group;

$Sum_{OL,(i+1)i}$ represents two sets of PET projection data corresponding to an axial overlapping region between the (i+1)-th bed and the i-th bed of the bed group; and $\omega_{i(i+1)}$ represents a weighting of $Sum_{OL,i(i+1)}$, $\omega_{(i+1)i}$ represents a weighting of $Sum_{OL,(i+1)i}$, wherein $\omega_{(i+1)i}+\omega_{i(i+1)}=1$, and $\omega_{(i+1)i},\omega_{i(i+1)}\in(0,1)$.

15. The device according to claim 9, wherein, for obtaining the PET multi-bed combined image by axially splicing the scaled PET images for the M bed groups together, said machine readable instructions further cause the processor to:

obtain an overlapping image for every two adjacent bed groups by performing a second weighted summing operation on a corresponding portion of the scaled PET images for every two adjacent bed groups that is corresponding to the axial non-overlapping region between the overlapping beds; and obtain the PET multi-bed combined image by axially splicing a corresponding portion of the scaled PET images for the M bed groups that is corresponding to the non-overlapping beds and the overlapping image for every two adjacent bed groups together.

16. The device according to claim 15, wherein, if the axial non-overlapping region between the overlapping beds includes a plurality of layers, said machine readable instructions further cause the processor to:

set weightings of a corresponding portion of the scaled PET images for axially-forward bed groups that is corresponding to the plurality of layers of the axial non-overlapping region of the overlapping beds to be decreased or unchanged with an increasing layer number; and set weightings of a corresponding portion of the scaled PET images for axially-rearward bed groups that is corresponding to the plurality of layers of the axial non-overlapping region of the overlapping beds to be increased or unchanged with the increasing layer number.

* * * * *